United States Patent [19]  [11] Patent Number: 4,954,325
Rubin et al.                    [45] Date of Patent: Sep. 4, 1990

[54] COMPOSITION OF SYNTHETIC POROUS CRYSTALLINE MATERIAL, ITS SYNTHESIS AND USE

[75] Inventors: Mae K. Rubin, Bala Cynwyd, Pa.; Pochen Chu, West Deptford, N.J.

[73] Assignee: Mobil Oil Corp., New York, N.Y.

[21] Appl. No.: 254,524

[22] Filed: Oct. 6, 1988

Related U.S. Application Data

[63] Continuation-in-part of Ser. No. 98,176, Sep. 18, 1987, abandoned, which is a continuation-in-part of Ser. No. 890,268, Jul. 29, 1986, abandoned.

[51] Int. Cl.⁵ .............................................. C01B 33/26
[52] U.S. Cl. ...................................... 423/328; 502/64; 502/74
[58] Field of Search ............... 423/328, 329, 326, 327; 502/64, 74

[56] References Cited

U.S. PATENT DOCUMENTS

| 4,439,409 | 3/1984 | Puppe et al. | 502/60 |
| 4,664,898 | 5/1987 | Arika et al. | 423/328 |
| 4,717,560 | 1/1988 | Vaughan | 423/328 |
| 4,826,667 | 5/1989 | Zones et al. | 423/277 |

FOREIGN PATENT DOCUMENTS

| 0231860 | 8/1987 | European Pat. Off. | 423/277 |
| 0293032 | 11/1988 | European Pat. Off. | 502/64 |

*Primary Examiner*—Anthony McFarlane
*Attorney, Agent, or Firm*—Alexander J. McKillop; Charles J. Speciale; Dennis P. Santini

[57] ABSTRACT

This invention relates to a new synthetic porous crystalline material, a method for its preparation and use thereof in catalytic conversion of organic compounds. The new crystalline material exhibits a distinctive X-ray diffraction pattern and unusually large equilibrium adsorption capacities.

30 Claims, 5 Drawing Sheets

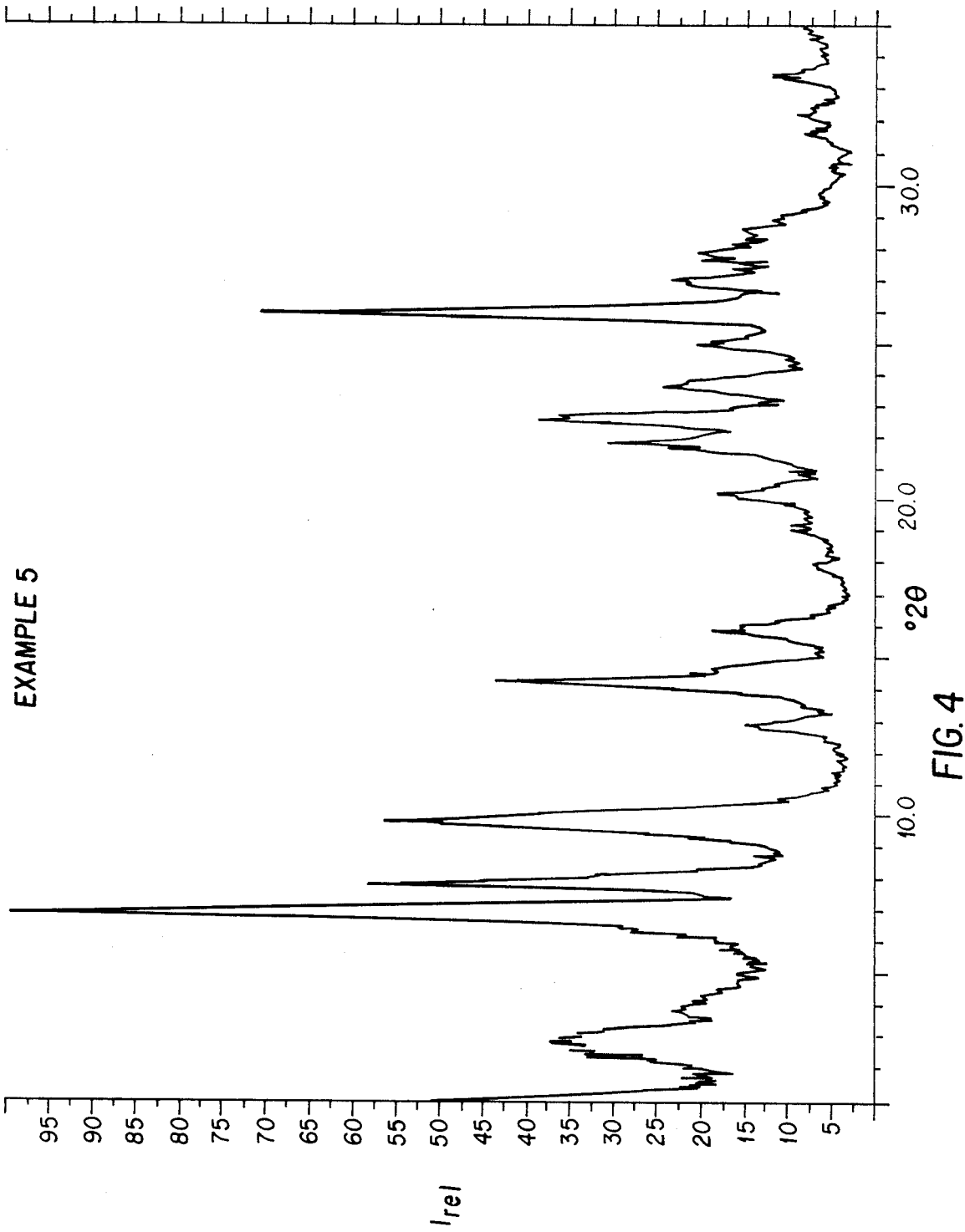

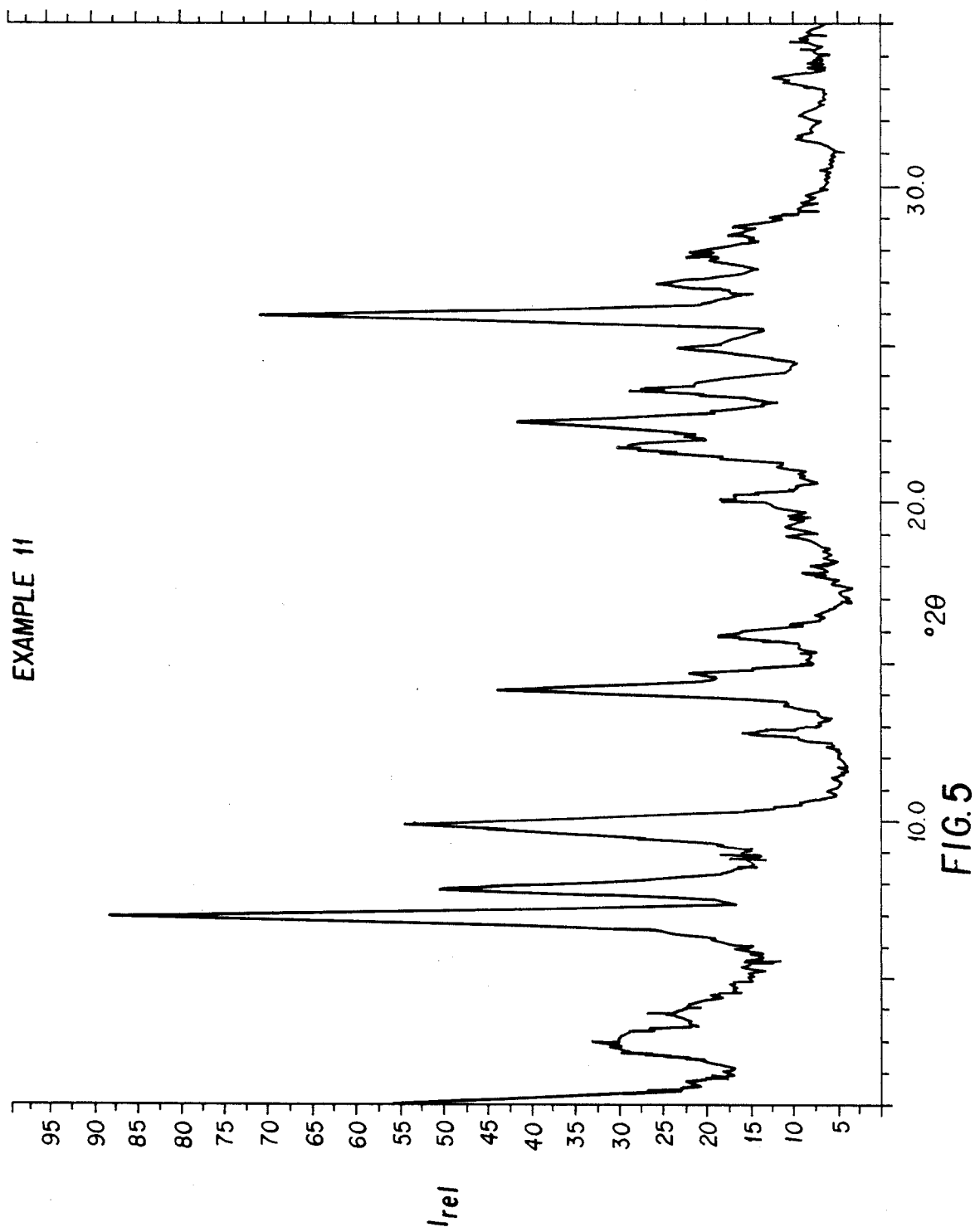

COMPOSITION OF SYNTHETIC POROUS CRYSTALLINE MATERIAL, ITS SYNTHESIS AND USE

CROSS-REFERENCE

This is a continuation-in-part of application Ser. No. 098,176, filed Sept. 18, 1987 now abandoned, which is a continuation-in-part of application Ser. No. 890,268, filed July 29, 1986 now abandoned.

BACKGROUND OF THE INVENTION

1. Field of the Invention

This invention relates to a novel composition of synthetic porous crystalline material, to a method for its preparation and to its use in catalytic conversion of organic compounds.

2. Description of the Prior Art

Zeolite materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline silicates. These silicates can be described as rigid three-dimensional framework of $SiO_4$ and Periodic Table Group IIIA element oxide, e.g. $AlO_4$, in which the tetrahedra are cross-linked by the sharing of oxygen atoms whereby the ratio of the total Group IIIA element, e.g. aluminum, and silicon atoms to oxygen atoms is 1:2. The electrovalence of the tetrahedra containing the Group IIIA element, e.g. aluminum, is balanced by the inclusion in the crystal of a cation, for example an alkali metal or an alkaline earth metal cation. This can be expressed wherein the ratio of the Group IIIA element, e.g. aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), ZSM-35 (U.S. Pat. No. 4,016,245), and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ and ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicate of varying alumina and metal content.

SUMMARY OF THE INVENTION

The present invention is directed to a novel composition of a porous crystalline material, a method for its preparation, and the conversion of organic compounds contacted therewith. The crystal prepared by this invention appears to be related to the compositions named "PSH-3" described in U.S. Pat. No. 4,439,409. The instant crystalline material does not appear to contain all the components apparently present in the PSH-3 compositions. The composition of this invention is not contaminated with other crystal structures, such as ZSM-12 or ZSM-5, exhibits unusual sorption capacities and unique catalytic utility when compared to the PSH-3 compositions synthesized in accordance with U.S. Pat. No. 4,439,409.

DESCRIPTION OF DRAWINGS

FIGS. 1–5 are X-ray diffraction patterns of the calcined crystalline material products of Examples 1, 3, 4, 5, and 11, respectively, hereinafter presented.

DESCRIPTION OF SPECIFIC EMBODIMENTS

Figure 1:
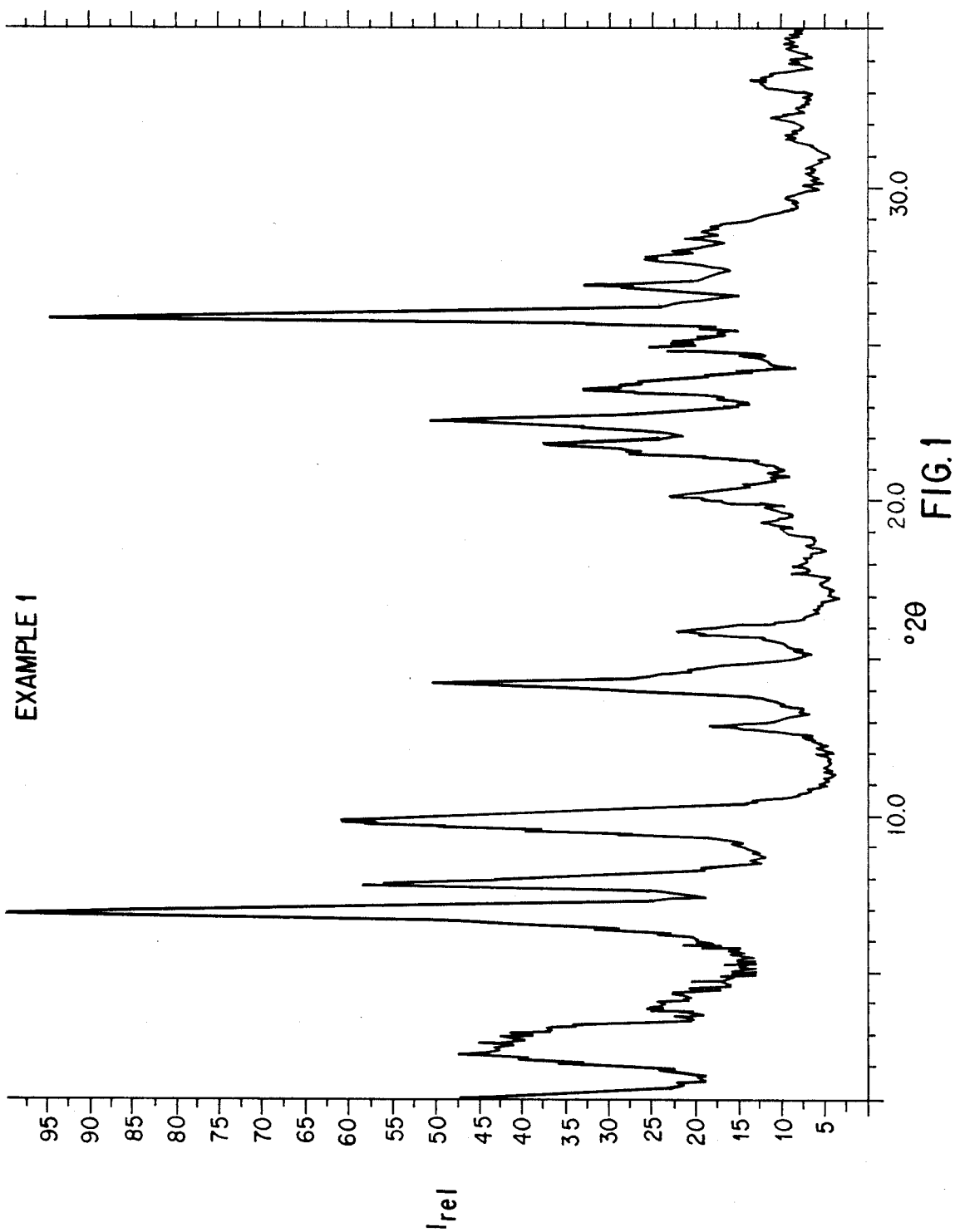

The crystalline material of this invention has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, the material has a formula, on an anhydrous basis and in terms of moles of oxides per n moles of $YO_2$, as follows:

$$(0.005-0.1)Na_2O:(1-4)R:X_2O_3:nYO_2$$

wherein R is an organic moiety. The Na and R components are associated with the material as a result of their presence during crystallization, and are easily removed by post-crystallization methods hereinafter more particularly described.

The crystalline material of the invention is thermally stable and exhibits high surface area (greater than 400 $m^2/gm$) and unusually large sorption capacity when compared to previously described crystal structures having similar X-ray diffraction patterns. As is evident from the above formula, the crystalline material of this invention is synthesized nearly free of Na cations. It can, therefore, be used as a catalyst with acid activity without an exchange step. To the extent desired, however, the original sodium cations of the as-synthesized material can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In its calcined form, the crystalline material of the invention appears to be made up of a single crystal phase with little or no detectable impurity crystal phases and has an X-ray diffraction pattern which is distinguished from the patterns of other known crystalline materials by the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W | more specifically by the lines listed in Table II below:

TABLE II

| Interplanar d-Spacing (A) | Relative Intensity, I/Io × 100 |
|---|---|
| 30.0 ± 2.2 | W-M |
| 22.1 ± 1.3 | W |
| 3.91 ± 0.07 | M-VS | and yet more specifically by the lines listed in Table III below:

TABLE III

| Interplanar d-Spacing (A) | Relative Intensity, I/Io × 100 |
|---|---|
| 30.0 ± 2.2 | W-M |
| 22.1 ± 1.3 | W |
| 6.00 ± 0.10 | W-M |
| 4.64 ± 0.08 | W |
| 4.06 ± 0.07 | W-S |
| 3.91 ± 0.07 | M-VS |

Most specifically, the calcined crystalline material of the invention has an X-ray diffraction pattern which includes the lines listed in Table IV below:

TABLE IV

| Interplanar d-Spacing (A) | Relative Intensity, I/Io × 100 |
|---|---|
| 30.0 ± 2.2 | W-M |
| 22.1 ± 1.3 | W |
| 12.36 ± 0.2 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |

TABLE IV-continued

| Interplanar d-Spacing (A) | Relative Intensity, I/Io × 100 |
|---|---|
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/$I_o$, where $I_o$ is the intensity of the strongest line or peak, and d (obs.) the interplanar spacing in Angstrom Units (A), corresponding to the recorded lines, were determined. In Tables I-IV, the relative intensities are given in terms of the symbols W=weak, M=medium, S=strong and VS=very strong. In terms of intensities, these may be generally designated as follows:

W=0-20
M=20-40
S=40-60
VS=60-100

It should be understood that this X-ray diffraction pattern is characteristic of all the species of the present crystalline composition. The sodium form as well as other cationic forms reveal substantially the same pattern with some minor shifts in interplanar spacing and variation in relative intensity. Other minor variations can occur, depending on the Y to X, e.g. silicon to aluminum, ratio of the particular sample, as well as its degree of thermal treatment.

When used as a catalyst, the crystalline material of the invention should be subjected to thermal treatment to remove part of all of any organic constituent. The crystalline material can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g. aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline material, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C.

The thermal treated product is particularly useful in the catalysis of certain hydrocarbon conversion reactions.

The crystalline material of this invention, when employed either as an adsorbent or as a catalyst in an organic compound conversion process should be dehydrated, at least partially. This can be done by heating to a temperature in the range of 200° C. to 595° C. in an atmosphere such as air, nitrogen, etc. and at atmospheric, subatmospheric or superatomspheric pressures for between 30 minutes and 48 hours. Dehydration can also be performed at room temperature merely by placing the silicate in a vacuum, but a longer time is required to obtain a sufficient amount of dehydration.

The present invention crystalline material can be prepared from a reaction mixture containing sources of alkali or alkaline earth metal (M), e.g. sodium or potassium, cation, an oxide of trivalent element X, e.g. aluminum, an oxide of tetravalent element Y, e.g. silicon, an organic (R) directing agent, hereinafter more particularly described, and water, said reaction mixture having a composition, in terms of mole ratios of oxides, within the following ranges:

| Reactants | Useful | Preferred |
| --- | --- | --- |
| $YO_2/X_2O_3$ | 10–80 | 10–60 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5. |

In the present synthesis method, the source of $YO_2$ must be comprised predominately of solid $YO_2$, for example at least about 30 wt. % solid $YO_2$ is order to obtain the crystal product of the invention. When $YO_2$ is silica, the use of a silica source containing at least about 30 wt. % solid silica, e.g. Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micro) favors crystal formation from the above mixture and is a distinct improvement over the synthesis method taught in U.S. Pat. No. 4,439,409. If another source of oxide of silicon, e.g. Q-Brand (a sodium silicate comprised of about 28.8 wt. % $SiO_2$, 8.9 wt. % $Na_2O$ and 62.3 wt. % $H_2O$) is used, crystallization yields little or none of the crystalline material of this invention. Impurity phases of other crystal structures, e.g. ZSM-12, are prepared in the latter circumstance. Preferably, therefore, the $YO_2$, e.g. silica, source contains at least about 30 wt. % solid $YO_2$, e.g. silica, and more preferably at least about 40 wt. % solid $YO_2$, e.g. silica.

Crystallization of the present crystalline material can be carried out at either static or stirred condition in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered.

The organic directing agent for use in synthesizing the present crystalline material from the above reaction mixture is hexamethyleneimine which has the following structural formula:

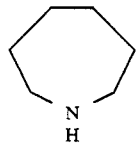

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

In all cases, synthesis of the new crystals is facilitated by the presence of at least 0.01 percent, preferably 0.10 percent and still more preferably 1 percent, seed crystals (based on total weight) of crystalline product.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material of this invention can be used to catalyze a wide variety of chemical conversion processes including many of present commercial/industrial importance. Specific examples of chemical conversion processes which are effectively catalyzed by the crystalline material of this invention, by itself or in combination with one or more other catalytically active substances including other crystalline catalysts, include the following:

(1) alkylation of aromatic hydrocarbons, e.g. benzene, with long chain olefins, e.g. $C_{14}$ olefin, with reaction conditions including a temperature of from about 340° C. to about 500° C., a pressure of from about atmospheric to about 200 atmospheres, a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(2) alkylation of aromatic hydrocarbons with gaseous olefins to provide short chain alkyl aromatic compounds, e.g. the alkylation of benzene with propylene to provide cumene, with reaction conditions including a temperature of from about 10° C. to about 125° C., a pressure of from about 1 to about 30 atmospheres, and an aromatic hydrocarbon weight hourly space velocity (WHSV) of from 5 $hr^{-1}$ to about 50 $hr^{-1}$;

(3) alkylation of reformate containing substantial quantities of benzene and toluene with fuel gas containing $C_5$ olefins to provide, inter alia, mono- and dialkylates with reaction conditions including a temperature of from about 315° C. to about 455° C., a pressure of from about 400 to about 800 psig, a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(4) alkylation of aromatic hydrocarbons, e.g. benzene, toluene, xylene and naphthalene, with long chain olefins, e.g. $C_{14}$ olefin, to provide alkylated aromatic lube base stocks with reaction conditions including a temperature of from about 160° C. to about 260° C. and a pressure of from about 350 to 450 psig;

(5) alkylation of phenols with olefins or equivalent alcohols to provide long chain alkyl phenols with reaction conditions including a temperature of from about 200° C. to about 250° C., a pressure of from about 200 to 300 psig and a total WHSV of from about 2 hr$^{-1}$ to about 10 hr$^{-1}$;

(6) conversion of light paraffins to olefins and aromatics with reaction conditions including a temperature of from about 425° C. to about 760° C. and a pressure of from about 10 to about 2000 psig;

(7) conversion of light olefins to gasoline, distillate and lube range hydrocarbons with reaction conditions including a temperature of from about 175° C. to about 375° C. and a pressure of from about 100 to about 2000 psig;

(8) two-stage hydrocracking for upgrading hydrocarbon streams having initial boiling points above about 500° F. to preimium distillate and gasoline boiling range products in a first stage using the crystalline material of this invention in combination with a Group VIII metal as catalyst with effluent therefrom being reaction in a second stage using zeolite Beta, also in combination with a Group VIII metal, as catalyst, the reaction conditions including a temperature of from about 340° C. to about 455° C., a pressure of from about 400 to about 2500 psig, a hydrogen circulation of from about 1000 to about 10,000 SCF/bbl and a liquid hourly space velocity (LHSV) of from about 0.1 to 10;

(9) a combination hydrocracking/dewaxing process in the presence of the crystalline material of this invention and a hydrogenation component as catalyst, or a mixture of such catalyst and zeolite Beta, with reaction conditions including a temperature of from about 350° C. to about 400° C., a pressure of from about 1400 to about 1500 psig, an LHSV of from about 0.4 to about 0.6 and a hydrogen circulation of from about 3000 to about 5000 SCF/bbl;

(10) reaction of alcohols with olefins to provide mixed ethers, e.g. the reaction of methanol with isobutene and/or isopentene to provide methyl-t-butyl ether (MTBE) and/or t-amyl methyl ether (TAM) with conversion conditions including a temperature of from about 20° C. to about 200° C., a pressure of from 2 to about 200 atm, a WHSV (gram-olefin per hour gram-zeolite) of from about 0.1 hr$^{-1}$ to about 200 hr$^{-1}$ and an alcohol to olefin molar feed ratio of from about 0.1/1 to about 5/1;

(11) toluene disproportionations with C$_9$+ aromatics as co-feed with reaction conditions including a temperature of from about 315° C. to about 595° C., a pressure of from about atmospheric to about 1000 psig, a hydrogen/hydrocarbon mole ratio of from about 0 (no added hydrogen) to about 10 and a WHSV of from about 0.1 hr$^{-1}$ to about 30 hr$^{-1}$;

(12) preparation of the pharmaceutically-active compound 2-(4-isobutylphenyl) propionic acid, i.e. ibuprofen, by reacting isobutylbenzene with propylene oxide to provide the intermediate 2-(4-isobutylphenyl) propanol followed by oxidation of the alcohol to the corresponding carboxylic acid;

(13) use as an acid-binding agent in the reaction of amines with heterocyclic fiber-reactive components in preparation of dyes to prepare practically salt-free reactive dye-containing solution, as in German Patent No. DE 3,625,693, incorporated entirely herein by reference;

(14) as the absorbent for separating 2,6-toluene diisocyanate (2,6-TDI) from isomers if TDI as in U.S. Pat. No. 4,721,807, incorporated entirely herein by reference, whereby a feed mixture comprising 2,6-TDI and 2,4-TDI is contacted with the present crystalline material which has been cation-exchanged with K ions to absorb the 2,6-TDI, followed by recovering the 2,6-TDI by desorption with desorbent material comprising toluene;

(15) as the absorbent for separating 2,4-TDI from its isomers as in U.S. Pat. No. 4,721,806, incorporated entirely herein by reference, whereby a feed mixture comprising 2,4-TDI and 2,6-TDI is contact with the present crystalline material which has been cation-exchanged with Na, Ca Li and/or Mg ions to absorb the 2,4-TDI, followed by recovering the 2,4-TDI by desorption with desorbent material comprising toluene; and

(16) in a process for decreasing the durene content of a 200°–400° F.+ bottoms fraction obtained from the catalytic conversion of methanol to gasoline which comprises contacting said durene-containing bottoms fraction with hydrogen over a catalyst of the present crystalline material with a hydrogenation metal, at conditions including a temperature of from about 230° C. to about 425° C. and a pressure of from about 50 psig to about 3000 psig.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples, whenever sorption data are set forth for comparison of sorptive capacities for water, cyclohexane and/or n-hexane, they were Equilibrium Adsorption values determined as follows:

A weighed sample of the calcined absorbant was contact with the desired pure absorbate vapor in an adsorption chamber, evacuated to less than 1 mm and contacted with 12 Torr of water vapor and 40 Torr of n-hexane or cyclohexane vapor, pressures less than the vapor-liquid equilibrium pressure of the respective absorbate at 90° C. The pressure was kept constant (within about ±0.5 mm) by addition of adsorbate vapor controlled by a manostat during the absorption period, which did not exceed about 8 hours. As adsorbate was adsorbed by the new crystal, the decrease in pressure caused the manostat to open a valve which admitted more absorbate vapor to the chamber to restore the above control pressures. Sorption was complete when the pressure change was not sufficient to activate the manostat. The increase in weight was calculated as the adsorption capacity of the sample in g/100 g of calcined adsorbant. The new synthetic material of this invention always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are notable distinguishing feature of the present crystalline material.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078 and in the *Journal of Catalysis*, vol. IV, pp. 522–529 (August 1965), each incorporated herein as to that description. It is noted that intrinsic rate constants for many acid-catalyzed reactions are proportional to the Alpha Value for a particular crystalline silicate catalyst, i.e. the rates for toluene disproportionation, xylene isomerization, alkene conversion and methanol conversion (see "The Active Site of Acidic Aluminosilicate Catalysts," *Nature*, Vol. 309, No. 5969, pp. 589–591, June 14, 1984).

EXAMPLE 1

Sodium aluminate (43.5% $Al_2O_3$, 32.2% $Na_2O$, 25.6% $H_2O$), 12.86 g, was dissolved in a solution containing 12.8 g 50% NaOH solution and 1320 g $H_2O$. To this was added 57.6 g hexamethyleneimine. The resulting solution was added to 109.4 g of Ultrasil, a precipitated, spray-dried silica (about 90% $SiO_2$).

The reaction mixture had the following composition, in mole ratios:

$SiO_2/Al_2O_3 = 30.0$;
$OH^-/SiO_2 = 0.18$;
$H_2O/SiO_2 = 44.9$;
$Na/SiO_2 = 0.18$;
$R/SiO_2 = 0.35$;

where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C. the X-ray diffraction pattern contained the major lines listed in Table V. FIG. 1 shows the X-ray diffraction pattern of the calcinated product. The sorption capacities of the calcined material were measured to be:

$H_2O$ (12 Torr): 15.2 wt. %;
Cyclohexane (40 Torr): 14.6 wt. %;
n-Hexane (40 Torr): 16.7 wt. %.

The surface area of the calcined crystalline material was measured to be 494 m$^2$/g.

The chemical composition of the uncalcined material was determined to be as follows:

| Component | wt % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio = | 21.1 |

TABLE V

| Degrees 2 Theta | Interplanar d-Spacing (A) | I/I$_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 19.08 | 4.65 | 2 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 25.01 | 3.56 | 20 |
| 26.00 | 3.43 | 100 |
| 26.96 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test, and found to have an Alpha Value of 224.

EXAMPLES 3-5

Figure 2:
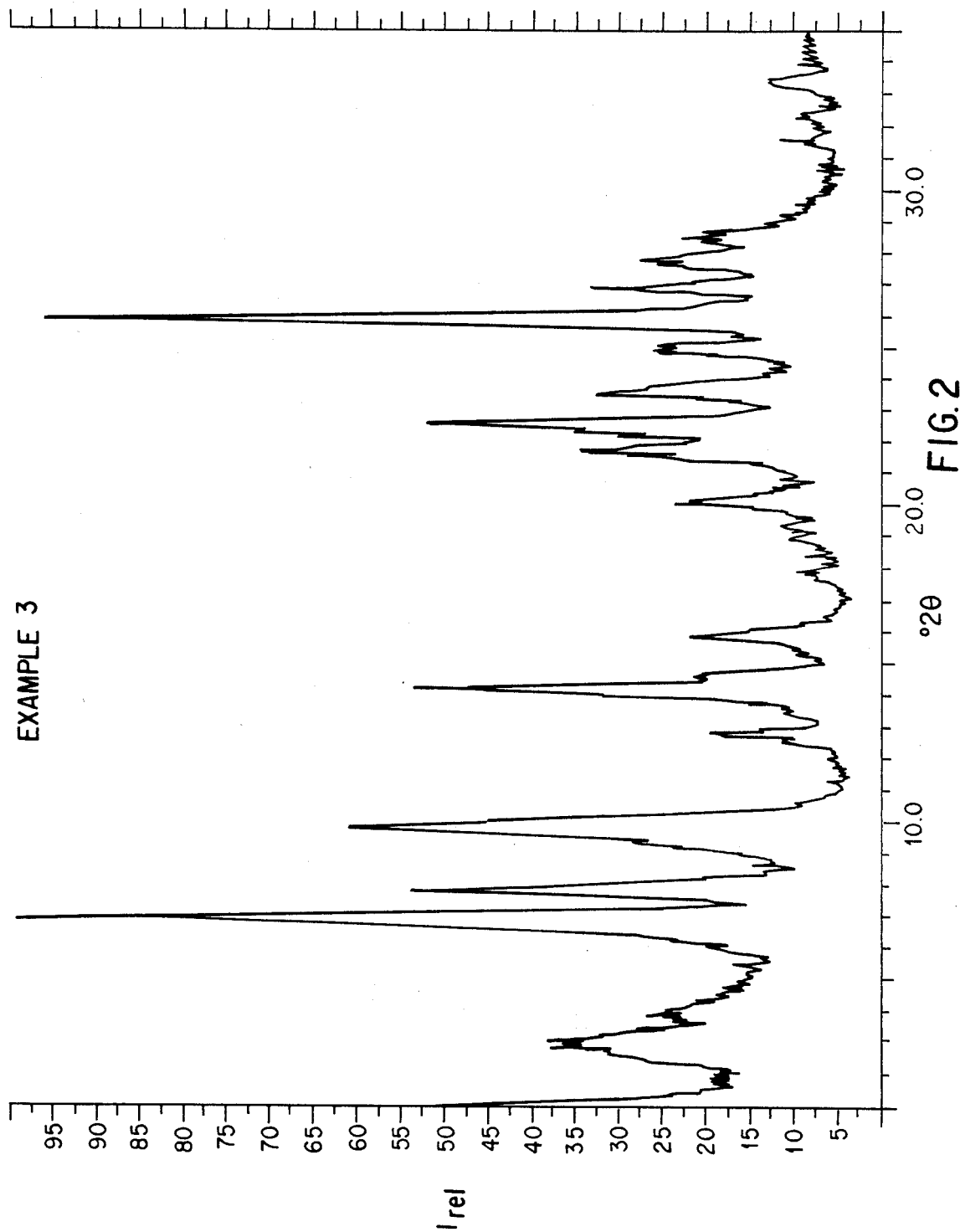
Figure 3:
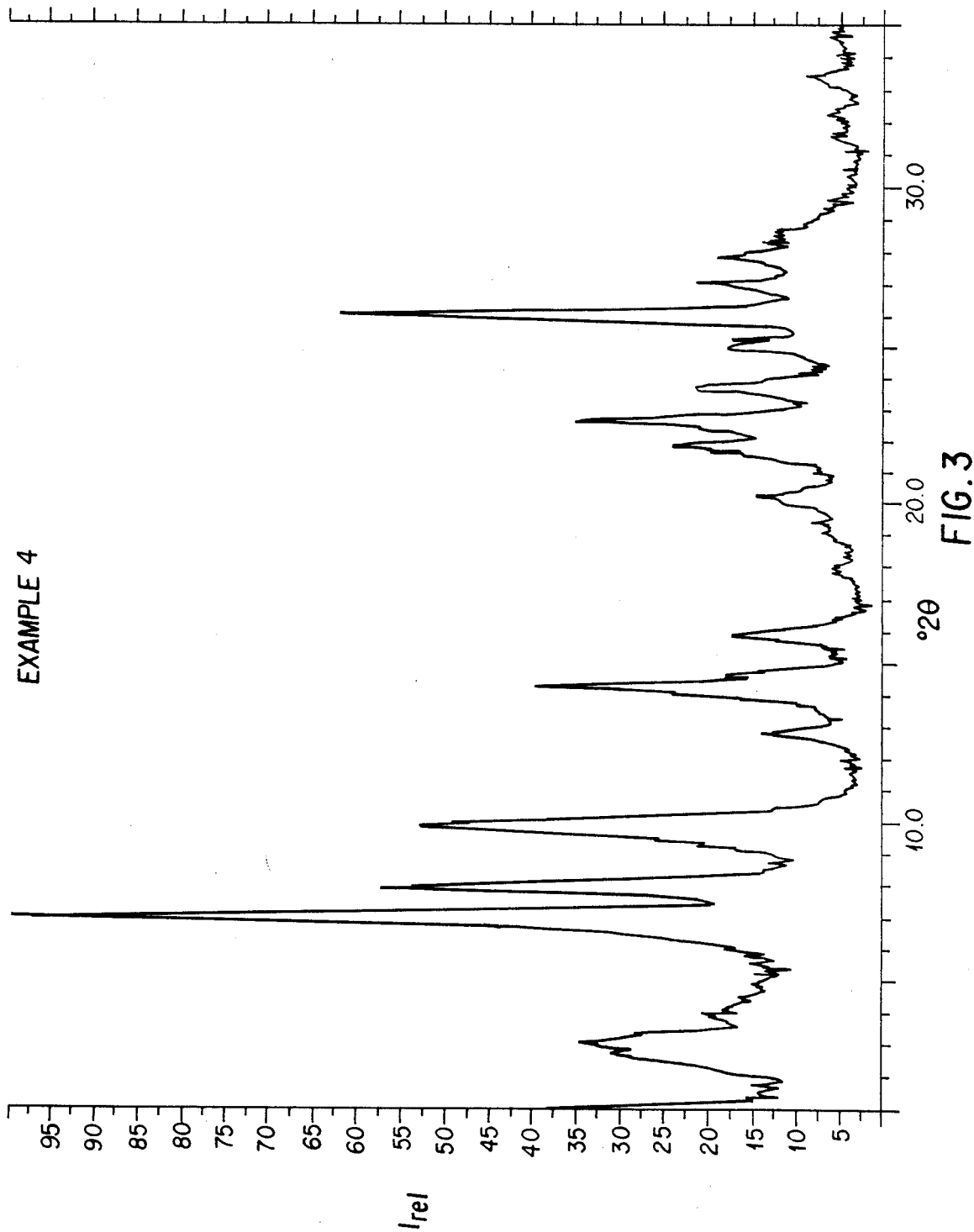

Three separate synthesis reaction mixtures were prepared with compositions indicated in Table VI. The mixtures were prepared with sodium aluminate, sodium hydroxide, Ultrasil, hexamethylene (R) and water. The mixtures were maintained at 150° C., 143° C. and 150° C., respectively, for 7, 8 and 6 days, respectively, in a stainless steel, stirred (350 rpm) autoclave at autogenous pressure. Solids were separated from any unreacted components by filtration and then water washed, followed by drying at 120° C. The product crystals were analyzed by X-ray diffraction, sorption, surface area and chemical analyses. The products were found to be the new crystalline material of the present invention. Results of sorption, surface area and chemical analyses are also presented in Table VI. The X-ray diffraction patterns of the calcined (538° C. for 3 hours) products of Examples 3, 4, and 5 are presented in FIGS. 2, 3, and 4, respectively. The sorption and surface area measurements were of the calcined product.

TABLE VI

| Example Number | 3 | 4 | 5 |
|---|---|---|---|
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test, and found to have Alpha Values of 227, 180 and 187, respectively.

EXAMPLE 7

A calcined sample of the crystalline silicate of Example 4 was impregnated with $Pt(NH_3)_4Cl_2$ solution to about 1 wt. % Pt. This material was then heated in air at 349° C. for 3 hours.

EXAMPLE 8

One gram of the resulting product from Example 7 was charged as catalyst to a small reactor with a preheater and imbedded thermocouple. The catalyst was then heated at 482° C. with flowing hydrogen to reduce the Pt component. Normal decane and hydrogen were charged over the catalyst to give 0.4 $hr^{-1}$ WHSV in decane and a hydrogen/hydrocarbon molar ratio of 100/1. The reaction was carried out in the temperature range of 130°-250° C. and atmospheric pressure.

The results of this experiment are summarized in Table VII, together with results of the same experiment, but with the crystalline material being changed to ZSM-5 (U.S. Pat. No. 3,702,886), ZSM-11 (U.S. Pat. No. 3,709,979) and Zeolite Beta (U.S. Pat. No. 3,308,069), presented for comparative purposes. It is observed that the crystalline silicate of the present invention is a very active catalyst for n-decane hydroconversion and has good isomerization activity. In Table VII, "5MN/2MN" is the molecular ratio of 5-methylnonane/2-methylnonane. Due to the position of its methyl group, 5-methylnonane offers slightly higher steric hindrance to enter zeolitic pores. The 5MN/2MN ratio provides information about the porosity of the zeolite being tested.

TABLE VII

| Catalyst Zeolite | $SiO_2/Al_2O_3$ Mole Ratio of Zeolite | Temp. (°C.) for 50% Conversion | % Isom. at 50%. Conversion | 5MN/2MN 5% Isom. | 5MN/2MN 20% Isom. |
|---|---|---|---|---|---|
| Example 7 | 20.9 | 174 | 70 | 0.15 | 0.24 |
| ZSM-5 | 50 | 187 | 65 | 0.11 | 0.15 |
| ZSM-11 | 40 | 187 | 94 | 0.36 | 0.41 |
| ZSM-23 | 85 | 211 | 90 | 0.27 | 0.28 |
| Beta | 30 | 189 | 76 | 0.68 | 0.59 |

EXAMPLE 9

In a glass reactor, a catalyst composed of a 0.2 g sample of the product of Example 4, calcined at 538° C. in air for 3 hours, was heated to 260° C. A mixture of 1,3,5-triethylbenzene and benzene in 10/90 weight ratio was charged into the reactor at the rate of 2 ml/hour together with nitrogen carrier gas. Reaction conditions were maintained at 260° C., atmospheric pressure and 10 $hr^{-1}$ WHSV. The results for this catalyst as well as other catalysts, for comparative purposes, are compared in Table VIII. The 1,3,5-triethylbenzene was in part isomerized (to 1,2,4-TEB) and in part transalkylated (to EB, DEB) over the present catalyst. The other catalysts give significantly different activity and selectivity.

TABLE VIII

| Catalyst | $SiO_2/Al_2O_3$ Mole Ratio of Zeolite | % Conversion Isomerization | % Conversion Transalkylation | Catalyst Alpha Value |
|---|---|---|---|---|
| ZSM-5 | 40 | 100 | 0 | 350 |
| ZSM-11 | 40 | 96 | 4 | 350 |
| Example 9 | 20.9 | 23 | 77 | 180 |
| Beta | 30 | 0 | 100 | 200 |
| Quartz | — | 0 | 0 | 1 |
| Alumina | — | 0 | 0 | 1 |

EXAMPLE 10

A 0.2 g sample of the crystalline product of Example 1, calcined at 538° C. for 3 hours, was tested for toluene disproportionation. The test conditions were 5 hr$^{-1}$ WHSV, atmospheric pressure and 260° C., 316° C. and 371° C. respectively. Toluene conversions of 10, 25 and 29.1%, respectively, were observed. The products were mainly benzene and xylenes with trace amounts of lighter and heavier by-products.

EXAMPLE 11

To demonstrate a larger preparation of the crystalline material of this invention, 1200 g of hexamethyleneimine was added to a solution containing 268 g of sodium aluminate, 267 g of 50% NaOH solution and 11,800 g of $H_2O$. To the combined solution was added 2,280 g of Ultrasil silica. The mixture was crystallized with agitation (about 200 rpm) at 145° C. in a 5 gallon reactor. Crystallization time was 59 hours. The product was water washed and dried at 120° C.

The X-ray diffraction pattern of the calcined (538° C.) product crystals is presented in FIG. 5 and demonstrates the product to be the crystalline material of this invention. Product chemical composition, surface area and adsorption analyses results were as follows:

TABLE IX

| Product Composition (uncalcined) | |
|---|---|
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| n-Hexane | 14.9 |
| $H_2O$ | 16.8 |
| Surface Area, m$^2$/g | 479 |

EXAMPLE 12

A 25 g quantity of solid crystal product from Example 11 was calcined in a flowing nitrogen atmosphere at 538° C. for 5 hours, followed by purging with 5% oxygen gas (balance $N_2$) for another 16 hours at 538° C.

Individual 3 g samples of the calcined material were ion-exchanged with 100 ml of 0.1N TEABr, TPABr and $LaCl_3$ solution separately. Each exchange was carried out at ambient temperature for 24 hours and repeated three times. The exchanged samples were collected by filtration, water-washed to be halide free and dried. The compositions of the exchanged samples are tabulated below demonstrating the exchange capacity of the present crystalline silicate for different ions.

| Exchange Ions | TEA | TPA | La |
|---|---|---|---|
| Ionic Composition, wt. % | | | |
| Na | 0.095 | 0.089 | 0.063 |
| N | 0.30 | 0.38 | 0.03 |
| C | 2.89 | 3.63 | — |
| La | — | — | 1.04 |

EXAMPLE 13

The above La-exchanged sample was sized to 14 to 25 mesh and then calcined in air at 538° C. for 3 hours. The calcined material had an Alpha Value of 173.

EXAMPLE 14

The calcined sample of La-exchanged material from Example 13 was severely steamed at 649° C. in 100% steam for 2 hours. The steamed sample had an Alpha Value of 22, demonstrating that the crystalline silicate hereof has very good stability under severe hydrothermal treatment.

EXAMPLE 15

To prepare the present crystal with X comprising boron, 17.5 g quantity of boric acid was added to a solution containing 6.75 g of 45% KOH solution and 290 g $H_2O$. To this was added 57.8 g of Ultrasil silica, and the mixture was thoroughly homogenized. A 26.2 g quantity of hexamethyleneimine was added to the mixture.

The reaction mixture had the following composition in mole ratios:

$SiO_2/B_2O_3=6.1$;
$OH^-/SiO_2=0.06$;
$H_2O/SiO_2=19.0$;
$K/SiO_2=0.06$;
$R/SiO_2=0.30$;

where R is hexamethyleneimine.

The mixture was crystallized in a stainless steel reaction, with agitation, at 150° C. for 8 days. The crystalline product was filtered, washed with water and dried at 120° C. A portion of the product was calcined for 6 hours at 540° C. and found to have the following sorption capacities:

$H_2O$ (12 Torr): 11.7 wt. %;
Cyclohexane (40 Torr): 7.5 wt. %;
n-Hexane (40 Torr): 11.4 wt. %.

The surface area of the calcined crystalline material was measured to be 405 m$^2$/g.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = | 1406 |
| $SiO_2/(Al + B)_2O_3$, molar ratio = | 25.8 |

EXAMPLE 16

A portion of the calcined crystalline product of Example 15 was treated with $NH_4Cl$ and again calcined. The final crystalline product was tested in the Alpha Test and found to have an Alpha Value of 1.

EXAMPLE 17

To prepare the present crystalline material with X comprising boron, 35.0 g quantity of boric acid was added to a solution of 15.7 g of 50% NaOH solution and 1160 g $H_2O$. To this solution was added 240 g of HiSil silica followed by 105 g of hexamethyleneimine. The reaction mixture had the following composition in mole ratios:

$SiO_2/B_2O_3=12.3$;
$OH^-/SiO_2=0.056$;
$H_2O/SiO_2=18.6$;
$Na/SiO_2=0.056$;
$R/SiO_2=0.30$;

where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured to be:

$H_2O$ (12 Torr): 14.4 wt. %;
Cyclohexane (40 Torr): 4.6 wt. %;
n-Hexane (40 Torr): 14.0 wt. %.

The surface area of the calcined crystalline material was measured to be 438 $m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = | 249 |
| $SiO_2/(Al + B)_2O_3$, molar ratio = | 28.2 |

EXAMPLE 18

A portion of the calcined crystalline product of Example 17 was tested in the Alphat Test and found to have an Alpha Value of 5.

EXAMPLE 19

To demonstrate additional differences between the present synthetic crystalline material and the product compositions of U.S. Pat. No. 4,439,409, the sorption capacities for a composition prepared according to U.S. Pat. No. 4,439,409 are listed in Table X. Also listed in Table X are the sorption capacities for the present products of Examples 1, 3–5, 11 and 15. Comparison of these measurements, all Equilibrium Adsorption measurements, indicates a rather large difference between the PSH-3 compositions prepared as in U.S. Pat. No. 4,439,409 and the present crystals.

TABLE X

| Example | 1 | 3 | 4 | 5 | 11 | 15 | '409 Patent PSH-3 |
|---|---|---|---|---|---|---|---|
| Equilibrium Adsorption, Wt. % | | | | | | | |
| $H_2O$ | 15.2 | 14.9 | 13.6 | 14.6 | 16.8 | 11.7 | 7.7 |
| Cyclohexane | 14.6 | 12.5 | 12.2 | 13.6 | 9.1 | 7.5 | 6.1 |
| n-Hexane | 16.7 | 14.6 | 16.2 | 19.0 | 14.9 | 11.4 | 6.9 |

EXAMPLE 20

To demonstrate the present improved method for synthesis of crystalline material of this invention, the method of Example 3 was repeated, except with Q-Brand sodium silicate (containing only about 29 wt. % solid silica) used as the source of silicon oxide. In this example, 67.6 g of aluminum sulfate was dissolved in a solution of 38.1 g $H_2SO_4$ (96.1%) and 400 g water. The resulting solution was mixed with 120 g of hexamethyleneimine and added to a mixture of 712.5 g Q-Brand Sodium silicate (28.8% $SiO_2$ and 8.9% $Na_2O$) and 351 g water. The resulting mixture, having the following composition expressed in mole ratios:

$SiO_2/Al_2O_3 = 30.0$;
$OH^-/SiO_2 = 0.18$;
$H_2O/SiO_2 = 19.4$;
$Na/SiO_2 = 0.60$;
$R/SiO_2 = 0.35$;

was thoroughly mixed and crystallized with stirring in a stainless steel reactor at 246° C. for 8 days. The product solids were separated from unreacted components by filtration and then water washed, followed by drying at 120° C. The product was analyzed by X-ray diffraction and found to be a mixture of amorphous material, magadiite and mordenite. No crystals of the present invention were found.

EXAMPLES 21–23

Three separated syntheses demonstrated in U.S. Pat. No. 4,439,409 for synthesis of PSH-3 compositions were conducted.

In Example 21, corresponding to Example 1 of U.S. Pat. No. 4,439,409, a solution containing 49.5 g hexamethyleneimine and 316 ml water was added to a solution of 203 ml Q-Brand sodium silicate and 14.0 ml water and mixed thoroughly. A solution of 9.22 g $Al_2(SO_4)_3 \cdot 18H_2O$, 23.4 g concentrated $H_2SO_4$ and 460 ml water was added with stirring.

The mixture was crystallized in a stirred (250 rpm) stainless steel autoclave at 150° C. for 72 hours, and the product was washed and dried at 120° C.

After calcination (500° C.), the product was shown to be composed of 0.23 parts $Na_2O$:61.9 parts $SiO_2$:1 part $Al_2O_3$. Its sorption properties were as follows:

$H_2O$: 5.7 wt. %;
Cyclohexane: 3.9 wt. %;
n-Hexane: 4.7 wt. %.

X-ray analysis proved the composition of Example 21 to be 4 parts crystalline ZSM-12 and only 1 part the present crystal.

In Example 22, corresponding to Example 4 of U.S. Pat. No. 4,439,409, a mixture of 31.2 g NaOH and 316 ml water was added to 260 g silica sol (30%). A 49.6 g quantity of hexamethyleneimine was added and the total thoroughly mixed. A solution containing 9.2 g $Al_2(SO_4)_3 \cdot 18H_2O$, 23.4 g $H_2SO_4$ and 460 ml water was added slowly. The final mixture was crystallized at 150° C. for 5 days with stirring. The product was washed and dried as above.

After calcination (500° C.), the product was shown to be composed of 0.21 parts $Na_2O$:69 parts $SiO_2$:1 part $Al_2O_3$. Sorption properties were of this composition were found to be:

$H_2O$: 6.4 wt. %;
Cyclohexane: 4.6 wt. %;
n-Hexane: 7.3 wt. %.

X-ray analysis proved the composition of Example 22 to be 4 parts the present crystal and 1 part crystalline ZSM-12.

In Example 23, corresponding to Example 6 of U.S. Pat. No. 4,439,409, the procedure of above Example 21 was repeated, except that 15.0 g $Al_2(SO_4) \cdot 18H_2O$ was used. After calcination at 500° C., the final product was shown to be composed of 0.02 parts $Na_2O$; 35.9 parts $SiO_2$:1 part $Al_2O_3$. Sorption capacities for this product composition proved to be:

$H_2O$: 9.7 wt. %;
Cyclohexane: 7.4 wt. %;
n-Hexane: 12.5 wt. %.

X-ray analysis proved the composition of Example 23 to be 5 parts crystalline ZSM-12, 4 parts crystalline ZSM-5 and only 1 part present crystal.

What is claimed is:

1. A synthetic porous crystalline material characterized by an X-ray diffraction pattern in its calcined form including values substantially as set forth in Table III of the specification and having equilibrium adsorption capacities of greater than about 10 wt. % for water vapor, greater than about 4.5 wt. % for cyclohexane vapor and greater than about 10 wt. % for n-hexane vapor.

2. The synthetic porous crystalline material of claim 1 characterized by an X-ray diffraction pattern including values substantially as set forth in Table IV of the specification.

3. The crystalline material of claim 1 having a composition comprising the molar relationship $$X_2O_3:(n)YO_2,$$

wherein n is at least about 10, X is a trivalent element and Y is a tetravalent element.

4. The crystalline material of claim 2 having a composition comprising the molar relationship $$X_2O_3:(n)YO_2,$$

wherein n is at least about 10, X is a trivalent element and Y is a tetravalent element.

5. The crystalline material of claim 1 having an as-synthesized composition, on an anhydrous basis and in terms of moles of oxides per n moles of $YO_2$, expressed by the formula:

$$(0.005 \text{ to } 0.1)Na_2O:(1 \text{ to } 4)R:X_2O_3:nYO_2$$

wherein R is an organic moiety, n is at least about 10, X is trivalent element and Y is a tetravalent element.

6. The crystalline material of claim 5 wherein said R is hexamethyleneimine.

7. The crystalline material comprising the crystalline material of claim 5 having original cations replaced, at least in part, with a cation of a mixture of cations selected from the group consisting of hydrogen and hydrogen precursors, rare earth metals, and metals of Groups IIA, IIIA, IVA, IB, IIB, IIIB, IVB, VIB and VIII of the Periodic Table of the Elements.

8. The crystalline material resulting from thermal treatment of the crystalline material of claim 5.

9. The crystalline material resulting from thermal treatment of the crystalline material of claim 7.

10. The crystalline material of claim 3 wherein n is from about 10 to about 150, X comprises aluminum and Y comprises silicon.

11. The crystalline material of claim 5 wherein n is from about 10 to about 150, X comprises aluminum and Y comprises silicon.

12. The crystalline material of claim 7 wherein said replacing cations comprise hydrogen or a hydrogen precursor.

13. The crystalline material of claim 9 wherein said replacing cations comprise metals.

14. A composition comprising the crystalline material of claim 1 and a matrix.

15. The composition of claim 14 wherein said matrix comprises alumina.

16. A method for preparing a synthetic crystalline material characterized by an X-ray diffraction pattern including values substantially as set forth in Table III of the specification and having equilibrium adsorption capacities of greater than about 10 wt. % for water vapor, greater than about 4.5 wt. % for cyclohexane vapor and greater than about 10 wt. % for n-hexane vapor, said crystalline material having a composition comprising the molar relationship $$X_2O_3:(n)YO_2$$

wherein n is at least about 10, X is a trivalent element and Y is a tetravalent element, said method comprising preparing a reaction mixture capable of forming said material upon crystallization, said reaction mixture containing sufficient amounts of alkali or alkaline earth metal cations, a source of tetravalent Y oxide containing at least about 30 wt. % solid $YO_2$, a source of trivalent X oxide, water and hexamethyleneimine, and maintaining said reaction mixture under sufficient crystallization conditions until crystals of said material are formed.

17. The method of claim 16 wherein said reaction mixture has a composition in terms of mole ratios within the following ranges:
$YO_2/X_2O_3 = 10$ to 80;
$H_2O/YO_2 = 5$ to 100;
$OH^-/YO_2 = 0.01$ to 1.0;
$M/YO_2 = 0.01$ to 2.0;
$R/YO_2 = 0.05$ to 1.0;
wherein R represents hexamethyleneimine and M represents alkali or alkaline earth metal.

18. The method of claim 17 wherein said reaction mixture has a composition in terms of mole ratios within the following ranges:
$YO_2/X_2O_3 = 10$ to 60;
$H_2O/YO_2 = 10$ to 50;
$OH^-/YO_2 = 0.1$ to 0.5;
$M/YO_2 = 0.1$ to 1.0;
$R/YO_2 = 0.1$ to 0.5.

19. The method of claim 16, wherein said reaction mixture further comprises a sufficient amount of crystal formation enhancing seed crystals.

20. A method for preparing a synthetic crystalline material characterized by an X-ray diffraction pattern including values substantially as set forth in Table III of the specification and having equilibrium adsorption capacities of greater than about 10 wt. % for water vapor, greater than about 4.5 wt. % for cyclohexane vapor and greater than about 10 wt. % for n-hexane vapor, said crystalline material having a composition comprising the molar relationship $$X_2O_3:(n)YO_2$$

wherein n is at least about 10 to about 150, X comprises aluminum and Y comprises silicon, said method comprising preparing a reaction mixture capable of forming said material upon crystallization, said reaction mixture containing sufficient amounts of alkali or alkaline earth metal cations, a source of silica containing at least about 30 wt. % solid silica, an oxide of aluminum, water and hexamethyleneimine, and maintaining said reaction mixture under sufficient crystallization conditions until crystals of said material are formed.

21. The method of claim 20 wherein said reaction mixture has a composition in terms of mole ratios within the following ranges:
$SiO_2/Al_2O_3 = 10$ to 80;
$H_2O/SiO_2 = 5$ to 100;
$OH^-/SiO_2 = 0.01$ to 1.0;
$M/SiO_2 = 0.01$ to 2.0;
$R/SiO_2 = 0.05$ to 1.0;
wherein R represents hexamethyleneimine and M represents alkali or alkaline earth metal.

22. The method of claim 21 wherein said reaction mixture has a composition in terms of mole ratios within the following ranges:

$SiO_2/Al_2O_3 = 10$ to 60;
$H_2O/SiO_2 = 10$ to 50;
$OH^-/SiO_2 = 0.1$ to 1.5;
$M/SiO_2 = 0.1$ to 1.0;
$R/SiO_2 = 0.1$ to 0.5.

23. The method of claim 20, wherein said reaction mixture further comprises a sufficient amount of crystal formation enhancing seed crystals.

24. The method of claim 20 wherein said solid silica source is a precipitated, spray dried silica.

25. The method of claim 21 wherein said solid silica source is a precipitated hydrated silica.

26. A synthetic porous crystalline material having the X-ray diffraction pattern of FIG. 1 after calcination.

27. A synthetic porous crystalline material having the X-ray diffraction pattern of FIG. 2 after calcination.

28. A synthetic porous crystalline material having the X-ray diffraction pattern of FIG. 3 after calcination.

29. A synthetic porous crystalline material having the X-ray diffraction pattern of FIG. 4 after calcination.

30. A synthetic porous crystalline material having the X-ray diffraction pattern of FIG. 5 after calcination.

* * * * *